United States Patent
Gradel et al.

(10) Patent No.: US 7,094,237 B2
(45) Date of Patent: Aug. 22, 2006

(54) VERTEBRAL COLUMN SUPPORT DEVICE WHICH IS ASSEMBLED BY MEANS OF CLAMPING

(75) Inventors: Thomas Gradel, Ayze (FR); Philippe Cottin, Saint Remy les Chevreuse (FR); Yves Jaby, Paris (FR); Jean-Philippe Lemaire, Saulon la Chapelle (FR)

(73) Assignee: Vitatech, Marignier (FR)

( * ) Notice: Subject to any disclaimer, the term of this patent is extended or adjusted under 35 U.S.C. 154(b) by 35 days.

(21) Appl. No.: 10/494,355

(22) PCT Filed: Oct. 23, 2002

(86) PCT No.: PCT/FR02/03623

§ 371 (c)(1),
(2), (4) Date: Apr. 27, 2004

(87) PCT Pub. No.: WO03/037198

PCT Pub. Date: May 8, 2003

(65) Prior Publication Data

US 2005/0010216 A1 Jan. 13, 2005

(30) Foreign Application Priority Data

Oct. 30, 2001 (FR) .................................. 01 14289

(51) Int. Cl.
*A61B 17/58* (2006.01)

(52) U.S. Cl. ....................................................... 606/61

(58) Field of Classification Search ............ 606/60–62, 606/64, 66, 72–73

See application file for complete search history.

(56) References Cited

U.S. PATENT DOCUMENTS

| | | | | |
|---|---|---|---|---|
| 4,648,388 A * | 3/1987 | Steffee | .......................... | 606/61 |
| 5,282,801 A * | 2/1994 | Sherman | ....................... | 606/61 |
| 5,643,263 A * | 7/1997 | Simonson | ..................... | 606/61 |
| 5,879,351 A * | 3/1999 | Viart | ............................ | 606/61 |
| 5,947,967 A * | 9/1999 | Barker | ......................... | 606/61 |
| 5,976,135 A * | 11/1999 | Sherman et al. | ............... | 606/61 |
| 6,106,526 A * | 8/2000 | Harms et al. | .................. | 606/61 |
| 6,183,473 B1 * | 2/2001 | Ashman | ....................... | 606/61 |
| 6,187,005 B1 * | 2/2001 | Brace et al. | ................... | 606/61 |
| 6,280,443 B1 * | 8/2001 | Gu et al. | ....................... | 606/61 |
| 6,309,390 B1 * | 10/2001 | Le Couedic et al. | .......... | 606/61 |

(Continued)

FOREIGN PATENT DOCUMENTS

EP 0408489 A1 1/1991

(Continued)

*Primary Examiner*—Eduardo C. Robert
*Assistant Examiner*—Annette Reimers
(74) *Attorney, Agent, or Firm*—William H. Eilberg

(57) ABSTRACT

A vertebral column support device is assembled by means of clamping. The device includes bone screw- or hook-type vertebrae anchoring elements, the elements consisting of a threaded cylindrical part (5) and a stop collar (7). A fixing nut (8) can be screwed on the threaded cylindrical part (5) in order to fix a connecting sliding piece (4) which is mounted on a securing rod (3) having a circular section. In order to insure that the rod (3) and the connecting sliding piece (4) are secure, the securing rod (3) is clamped in a transverse groove (17) in the connecting sliding piece (4) using a clamp screw (21) and a little clamp (22) which is mounted in the corner of the groove. In this way, the inventive device is more rigid and can better support the vertebrae and, moreover, the device can be positioned and adjusted much more easily.

11 Claims, 3 Drawing Sheets

U.S. PATENT DOCUMENTS

| | | |
|---|---|---|
| 6,520,962 B1 * | 2/2003 | Taylor et al. ............... 606/61 |
| 6,562,038 B1 * | 5/2003 | Morrison ................... 606/61 |
| 6,620,164 B1 * | 9/2003 | Ueyama et al. ............. 606/61 |
| 6,641,583 B1 * | 11/2003 | Shluzas et al. ............. 606/61 |
| 6,648,887 B1 * | 11/2003 | Ashman .................... 606/61 |
| 6,673,074 B1 * | 1/2004 | Shluzas .................... 606/61 |
| 6,676,661 B1 * | 1/2004 | Martin Benlloch et al. ... 606/61 |
| 6,685,705 B1 * | 2/2004 | Taylor ..................... 606/61 |
| 6,709,434 B1 * | 3/2004 | Gournay et al. ............ 606/61 |

FOREIGN PATENT DOCUMENTS

| | | |
|---|---|---|
| FR | 2720923 | 12/1995 |
| WO | WO-91/11967 | 8/1991 |
| WO | WO-00/15125 | 3/2000 |

* cited by examiner

VERTEBRAL COLUMN SUPPORT DEVICE WHICH IS ASSEMBLED BY MEANS OF CLAMPING

TECHNICAL FIELD OF THE INVENTION

The present invention relates to a device for supporting vertebrae in a required position. A device of this kind is used to treat a spine having an abnormal deviation of degenerative or traumatic origin.

For example, it is possible to treat vertebral fractures or arthroses, to correct vertebral column deviations such as scoliosis, lordosis and cyphosis.

The document U.S. Pat. No. 4,648,388 discloses a device for treatment of the spine comprising members adapted to be anchored in the vertebrae, a circular section securing rod having a smooth exterior surface, and sliding connecting members for connecting the anchor members and the securing rod. The anchor members are screws having three main portions, namely a first end portion with a helicoidal screwthread adapted to penetrate and to be retained in bone, a smooth cylindrical intermediate portion of smaller diameter, and a second end portion with a helicoidal screwthread onto which a clamping nut is screwed. The sliding connecting members have a clamping portion conformed to fit over a section of the securing rod, and a connecting portion projecting laterally and pierced by two holes adapted to have an anchor screw pass through them. The anchor screw is first screwed into the bone, the sliding connecting member is then fitted to the cylindrical intermediate portion of the anchor screw, and the clamping nut is finally screwed onto the second screwthreaded portion of the clamping screw to press the sliding connecting member against a vertebra and simultaneously to clamp the sliding connecting member around the securing rod.

A device of this kind is intended to support the spine with an appropriate curvature. The mechanical retention provided by the device is sometimes insufficient, however. In particular, the fact that the sliding member bears directly on a vertebra rules out effective clamping, because vertebrae have poor mechanical strength in compression, as a result of which there is a major risk of the sliding member slipping and rotating on the securing rod. Also, the above device is not suitable for three-dimensional reduction of the upper portion of the spine, where screws may not be implanted. Furthermore, the clamping force of the nut significantly increases the traction stress exerted on the screw, being added to the securing force exerted by the securing rod, which reduces commensurately the mechanical strength of the anchorage and encourages necrosis of the bone around the screw. Furthermore, when the sliding member is in position on the screw, it is no longer possible to engage the securing rod laterally in the sliding member.

The document EP-A-0 408 489 describes a device for connecting two vertebrae by means of two twin-thread pedicular screws and two sliding members connected by a threaded rod enabling the distance between them to be adjusted. The screw has an intermediate stop plate with a male spherical bearing surface for adjusting the inclination relative to the sliding member by partial engagement in a hole in the sliding member. Clamping a clamping nut onto the screwthreaded portion of the screw prevents rotation, the nut coming to bear on a washer placed against the sliding member. This device, which seems suitable for adjusting the spacing of two successive vertebrae, is totally unsuitable for supporting more than two vertebrae, and there is no teaching regarding the problem of the insufficient mechanical retention of smooth securing rods. What is more, when the sliding member is in position on the screw, it is no longer possible to engage the screwthreaded rod laterally.

The document WO 91 11967 describes a device for treatment of the spine comprising twin-thread pedicular screws and an intermediate stop plate, to which is attached a sliding member conformed to receive and retain a securing rod. The sliding member has a lower groove in which the stop plate is engaged to prevent it rotating relative to the screw, and a top groove in which the securing rod is engaged. The screwthreaded portion of the screw passes through the sliding member, and a locking nut with a frustoconical lower bearing surface is screwed onto the screwthreaded portion and forces the securing rod laterally into the top groove of the sliding member to immobilize it. The conical bearing surface of the nut, bearing on the cylindrical shape securing rod, cannot secure the securing rod sufficiently rigidly. What is more, when the sliding member is fixed to the screw by the nut, it is no longer possible to engage the securing rod laterally.

The document WO 00 15125 describes two other means of securing the rod to the sliding member. The first means comprise a grub screw with a conical end bearing on the side of the rod. The second means comprise a member pushed radially against the side of the rod by a screw. Neither of these securing means provides sufficient rigidity.

In the document FR 2 720 923, a locking nut with a spherical bearing surface comes to bear radially against the rod. For the same reasons as before, this does not provide sufficient rigidity.

SUMMARY OF THE INVENTION

The problem addressed by the present invention is that of designing a new structure of a device for treatment of the spine with a smooth securing rod and anchor members in the form of sliding connecting members, which device secures the vertebrae much more effectively and greatly facilitates fitting the component parts and adjusting their relative positions in three dimensions. One particular aim is to allow the securing rod to be engaged with and disengaged from a sliding member already in position on a screw or other anchor member by lateral displacement.

To this end, the device in accordance with the present invention for treatment of the spin comprises
- anchor members adapted to be anchored in vertebrae, each having a cylindrical screwthreaded portion onto which is screwed a clamping nut, and an anchor portion connected to the cylindrical screwthreaded portion by an intermediate stop flange,
- at least one circular section securing rod having a smooth exterior surface,
- sliding connecting members for connecting the anchor members to the securing rod, the sliding connecting members including a first hole conformed to have the cylindrical screwthreaded portion of an anchor member passed through it to fasten it to an anchor member, the sliding connecting members having a top transverse groove conformed to receive a section of the securing rod, with clamping means for selectively clamping and unclamping the securing rod in said transverse groove;

according to the invention, the clamping means comprise:
- a clamping screw, having a screwthreaded shank and a head,
- a clamping hole in the bottom of the transverse groove of the sliding member, separate from the first hole and offset laterally relative to the first hole, a cylindrical bearing surface constituting a first edge of the transverse groove and conformed to receive a section of the securing rod, an oblique bearing surface constituting an opposite edge of the transverse groove and inclined relative to the axis of the clamping hole, a clamping member in the corner of the transverse groove between the oblique bearing surface and the securing rod and adapted to be pushed toward the bottom of the transverse groove by the clamping screw, having a bearing face bearing and sliding on the oblique bearing surface, and having an opposite thrust face bearing on the securing rod to immobilize it in the transverse groove.

In one practical embodiment, the clamping member has a hole through it through which the clamping screw passes, so that the head of the clamping screw bears on the external face of the clamping member to push it toward the bottom of the transverse groove.

The clamping hole is preferably oriented obliquely to the axis of the first hole, in the direction approaching the axis of the first hole on screwing of the clamping screw.

To improve the rigid retention of the securing rod and facilitate lateral insertion of the securing rod into the sliding member, the thrust face has a plane lower portion oriented generally toward the bottom of the transverse groove to bear against the securing rod, and an upper portion open at the top to facilitate lateral engagement of the securing rod.

In an advantageous embodiment, to facilitate assembling the components of the device after fixing the anchor members to the spine, means are provided for orienting the sliding member on the corresponding anchor member. To this end, the stop flange has a male spherical bearing surface engaging in a corresponding female spherical surface at the entry of the first hole in the sliding connecting member, the first hole in the sliding connecting member having a diameter greater than the diameter of the cylindrical screwthreaded portion of the anchor member to allow angular oscillation of the sliding connecting member on the anchor member and away from the axis before clamping of the clamping nut.

The device may comprise anchor members in the form of one or more twin-thread bone screws on either side of an intermediate stop flange, one or more hooks whose rear wall serves as a stop flange, and where applicable bearing plates conformed to adapt to the particular morphology of certain regions of the spine.

BRIEF DESCRIPTION OF THE DRAWINGS

Other objects, features and advantages of the present invention will emerge from the following description of particular embodiments, which is given with reference to the appended drawings, in which.

DESCRIPTION OF THE PREFERRED EMBODIMENTS

Figure 1:
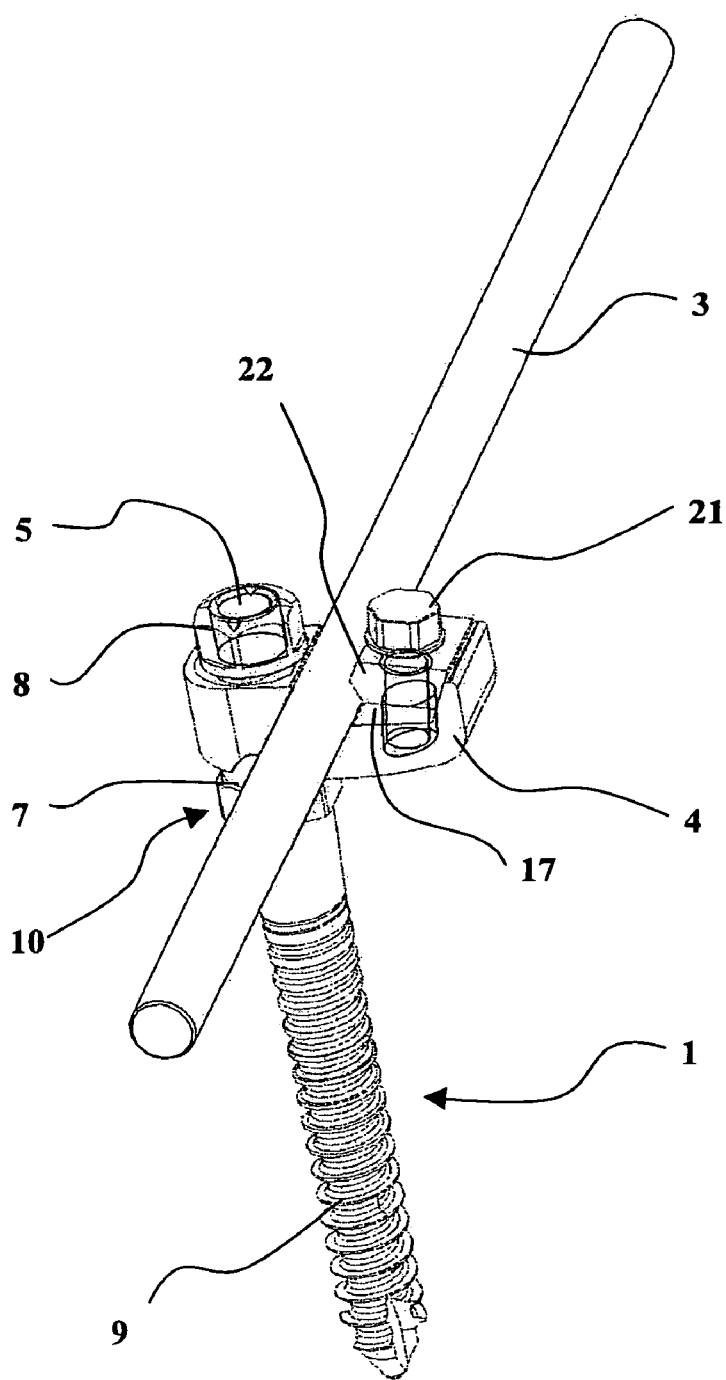
FIG. 1 is a perspective view of a bone screw that can be used as an anchor member in accordance with the invention, assembled to a sliding member and to a securing rod of a preferred embodiment.

The device represented in the drawings comprises anchor members such as bone screws 1 (FIGS. 1 and 2) or hooks 2 (FIG. 3), securing rods 3, and sliding connecting members 4 between each anchor member and the securing rod 3.

The securing rods 3 of the device according to the invention are smooth circular section rods. The material and the section are selected to obtain optimum elasticity, matched to the forces to be encountered in use, and so that the rod can be curved to the required shape of the vertebral column portion to be treated.

Each anchor member, bone screw 1, hook 2 or bearing plate, is in one piece with a screwthreaded cylindrical portion 5 having an exterior screwthread 6, and comprises a stop flange 7 delimiting the screwing of a clamping nut 8 onto the exterior screwthread 6.

Figure 2:
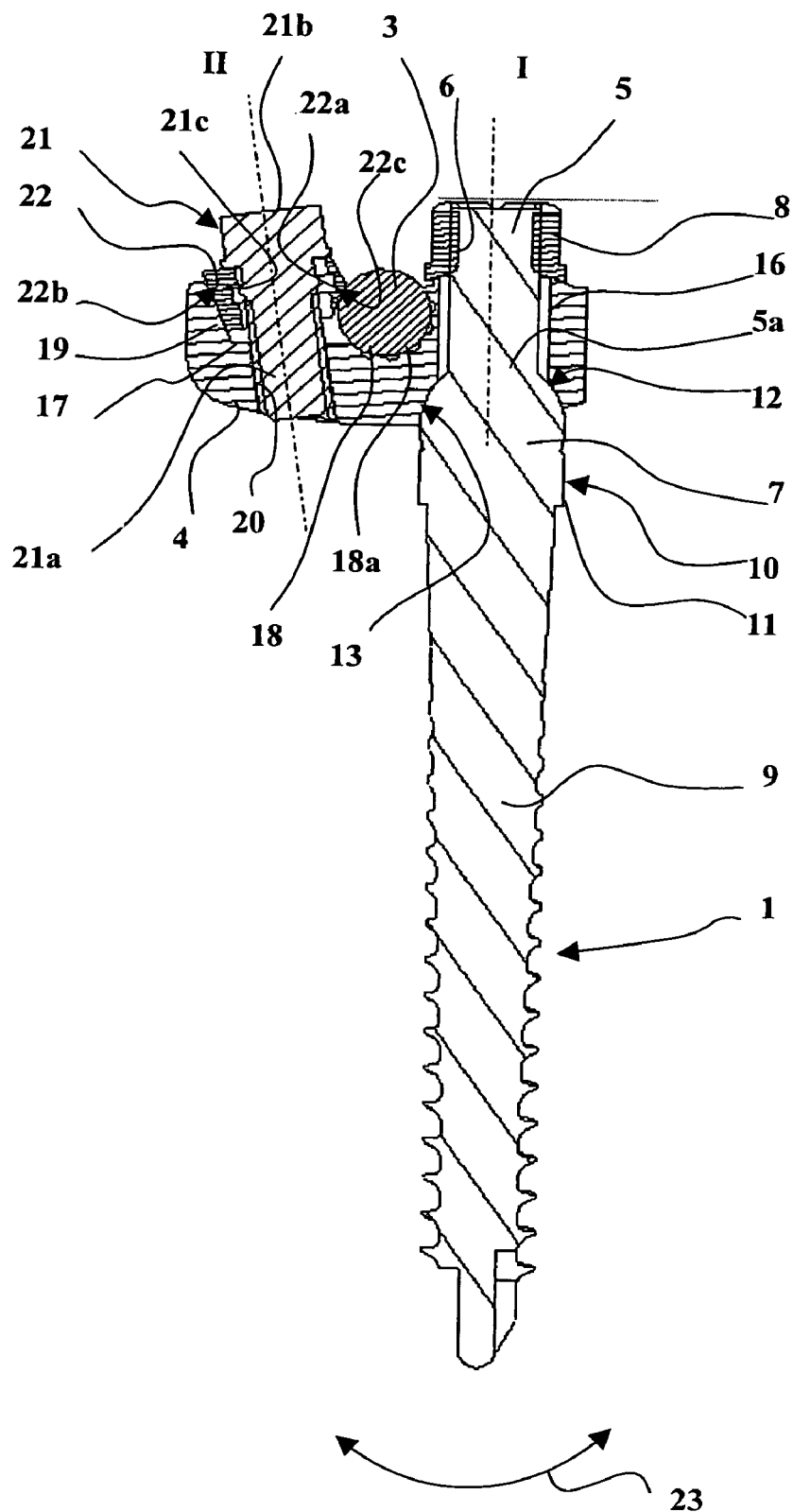
FIG. 2 is a view in cross section and to a larger scale of the assembly from FIG. 1.

In the embodiment shown in FIGS. 1 and 2, the anchor member is a twin-thread bone screw 1, the cylindrical screwthreaded portion 5 with the exterior screwthread 6 constituting the first screwthread, and a coaxial second screwthreaded portion 9, on the opposite side of the stop flange 7, constituting a second screwthread adapted to be screwed into bone. The stop flange 7 constitutes an intermediate portion of larger section between the two screwthreaded portions 5 and 9. The stop flange 7 advantageously has a peripheral surface 10 with six flat facets, an abutment surface 11 connecting to the coaxial second screwthreaded portion 9 and adapted to bear against the vertebral bone, and an opposite bearing surface 12 connected to the cylindrical screwthreaded part 5 and extending from its base 5*a*.

In the embodiment shown, the bearing surface 12 of the stop flange 7 is a convex spherical surface whose convex side faces the cylindrical screwthreaded portion 5, and constitutes a male spherical bearing surface adapted to engage in a corresponding female spherical surface 13 of the sliding connecting member 4.

It is known in the art that the cylindrical screwthreaded portion 5 may be extended by a coaxial surplus screwthreaded section 5*c* (shown in FIG. 3) to which it is connected by an intermediate annular groove 5*b* constituting a point of weakness to facilitate cutting off the surplus section after screwing a nut onto the cylindrical screwthreaded portion 5. The annular groove 5*b* advantageously has a sawtooth section, with the bottom of the groove adjoining the end of the cylindrical screwthreaded portion 5.

Figure 3:
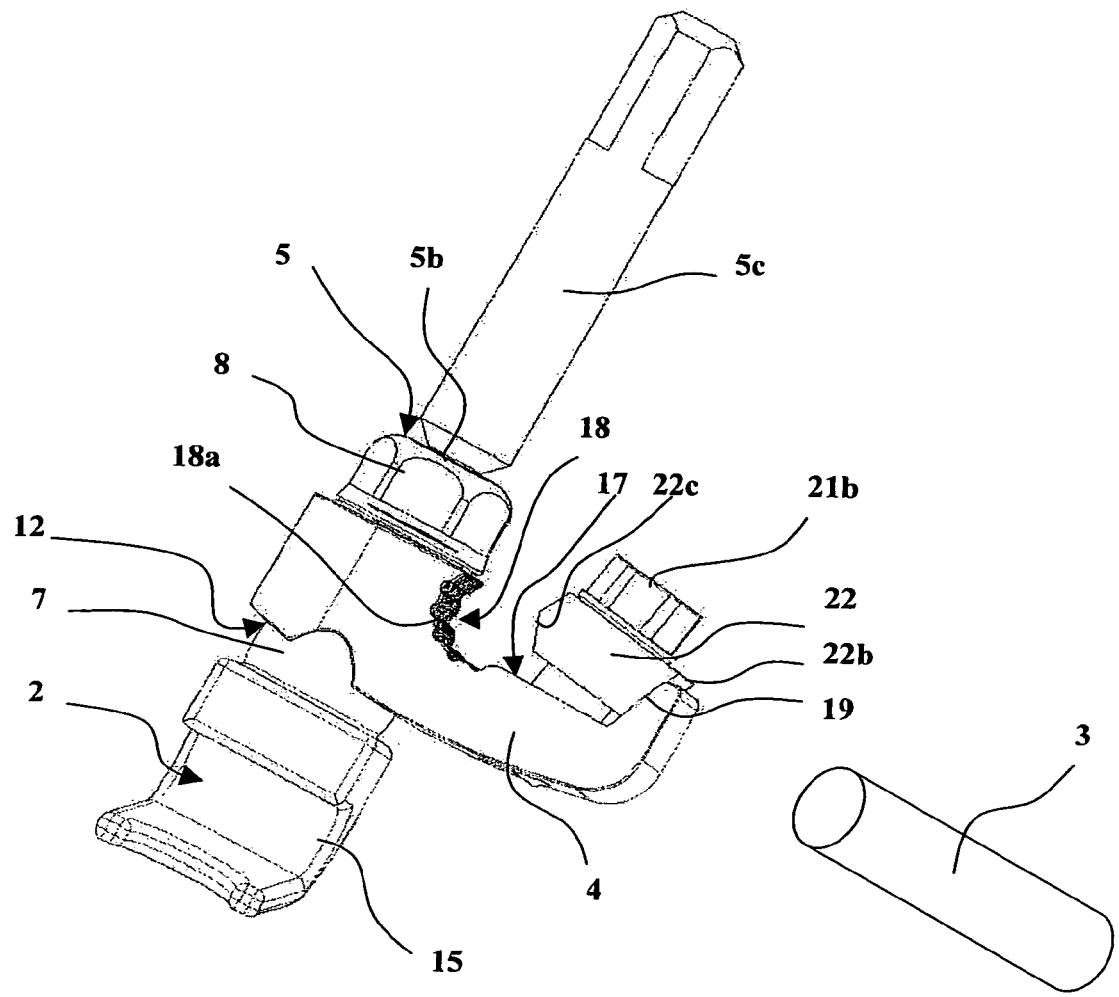
FIG. 3 is a perspective view of a lamina hook that may be used as an anchor member according to the invention, assembled to a sliding member for fitting to a securing rod.

In the FIG. 3 embodiment, the anchor member is a pedicular hook 2, adapted to hook onto a pedicle of a vertebra. The hook 2 has a hook body 15, that is curved as shown in the figure, and a bearing surface 12 to which the cylindrical screwthreaded portion 5 is connected. As in the FIG. 2 pedicular screw, the bearing surface 12 is a male spherical surface.

The sliding connecting member 4 includes a first hole 16 conformed to have the cylindrical screwthreaded portion 5 of an anchor member 1 or 2 passed through it, and a top transverse groove 17 conformed to receive a section of the securing rod 3. Clamping means are provided for selectively clamping and unclamping the securing rod 3 in the transverse groove 17.

The transverse groove 17 has a cylindrical bearing surface 18 that constitutes one of its edges and is conformed to receive the section of securing rod 3, for example wrapping approximately 120° around it as shown in FIG. 2. The cylindrical bearing surface 18 preferably has non-slip raised patterns 18*a* that effectively oppose movement of the securing rod 3 in the sliding connecting member 4 in translation or in rotation.

The opposite edge of the transverse groove 17 is an oblique bearing surface 19, that is inclined so that the transverse groove 17 widens toward the top.

The sliding connecting member 4 includes a tapped clamping hole 20, separate from the first hole 16, in the bottom of the transverse groove 17 of the sliding connecting member 4.

A clamping screw 21, with a screwthreaded shank 21*a* and a head 21*b*, screws into the clamping hole 20.

The clamping hole 20 is offset laterally relative to the first hole 16, and its axis II is preferably slightly oblique to the axis I of the first hole 16, the axes I and II defining an angle whose apex is directed downward, i.e. away from the transverse groove 17.

Thus the clamping hole 20 is oriented obliquely to the axis I of the first hole 16 in the direction toward the axis I of the first hole 16 upon screwing in the clamping screw 21.

The oblique bearing surface 19 that delimits the opposite edge of the transverse screw 17 is inclined and defines, with the axis II of the clamping hole 20, an angle whose apex is also directed downward.

A clamping member 22 is located in the corner of the transverse groove 17, between the oblique bearing surface 19 and the securing rod 3. The clamping member 22 is pushed toward the bottom of the transverse groove 17 by the clamping screw 21. To this end, there is a hole in the clamping member 22 through which the clamping screw 21 passes, so that the head 21*b* of the clamping screw 21 bears on the external face of the clamping member 22 to push it toward the bottom of the transverse groove 17.

The clamping member 22 preferably turns freely about the clamping screw 21, and is retained axially on the screwthreaded shank 21*a* of the clamping screw 21 by a flange 21*c* of the clamping screw 21 that is engaged in an oval annular groove 22*a* inside the hole in the clamping member 22.

The clamping member 22 has a bearing face 22*b* that bears and slides on the oblique bearing surface 19 of the sliding connecting member 4, and an opposite thrust face 22*c* bearing on the securing rod 3 to immobilize it in the transverse groove 17. The thrust face 22*c* advantageously has a plane lower portion that is oriented generally toward the bottom of the transverse groove 17 to bear against an upper portion of the securing rod 3, and an upper portion that is open at the top to facilitate lateral engagement of the securing rod 3.

The lower end of the first hole 16 is flared to constitute the female spherical surface 13 in which the male spherical bearing surface 12 of the stop flange 7 engages. The first hole 16 in the sliding connecting member 4 otherwise has a diameter greater than the diameter of the screwthreaded cylindrical portion 5 of the anchor member 1 or 2, to allow angular oscillation of the sliding connecting member 4 away from the axis I on the anchor member 1 or 2 before clamping the clamping nut 8. This oscillation is symbolized by the double-headed arrow 23 in FIG. 2.

In the embodiment shown in the figures, the securing rod 3 is engaged in the transverse groove 17 in an intermediate position between the clamping screw 21 and the portion with the first hole 16 to receive the screwthreaded cylindrical portion 5 of the anchor member 1 or 2.

The device of the invention allows the use of a rod or a plurality of rod members with a curvature appropriate to the vertebral region to be treated.

The sliding connecting members 4 are easy to fit to the securing rod 3, as they can be threaded over each of its ends, or fitted by lateral engagement, and slide freely on the securing rod 3 regardless of its curvature.

The principle of reduction of the deformed spine is three-dimensional. It is necessary to transform a scoliotic curve oriented in a plane close to the frontal plane into a curve of physiological shape situated in the sagittal plane and having normal lumbar lordotic, thoracic and cyphotic curvature.

First of all a shape close to the normal physiological curvature is imparted to the securing rod, which is positioned in the sagittal plane of the patient, with its two ends fixed by correctly clamped anchor members and sliding members. The non-slip raised patterns on the sliding members immobilize the rod very effectively, both in translation and, most importantly, in rotation. Anchor members are fitted into or onto the other intermediate vertebrae. The anchorages closest to the rod are engaged in the sliding members and locked by immobilizing the rod in the sagittal plane and in rotation by clamping the clamping screw. Engagement of the anchorages farthest from the rod and on the concave side of the curve is catered for by the length of the cylindrical screwthreaded portion 5 of the anchor members. Once the end of the cylindrical screwthreaded portion has been inserted into the bore of a sliding connecting member 4 that is itself fixed to the rod, gradual clamping of the clamping nut 8 moves the anchor point toward the securing rod, progressively reducing the vertebral curvature. If the elasticity of the spine is used up, the securing rod 3 is deformed, and provides a correction in an intermediate position of maximum reduction.

The device of the invention therefore enables each intermediate anchor member to be processed in place, by introducing its cylindrical screwthreaded portion into the bore of a sliding member, and fixing it rigidly to the rod, in alignment with the anchor members above and below it, to obtain the required straightening of the vertebrae fitted out in this way.

The device constituting the subject matter of the invention may equally well be fitted to the spine of the patient in an anterior position or in a posterior position, relative to the spine.

The device according to the invention may be fitted in a much shorter operating time than prior art devices, given the increased ease with which the surgeon may offer up the components of the device to each other and to the spine and assemble them.

Clearly, according to the spinal treatment to be carried out, the device according to the invention may comprise anchoring screws, anchoring hooks, or anchoring plates, or a combination of two or three of these types of anchoring, which are thus independent of each other.

The anchor members may in particular take the form of one or more twin-thread bone screws, the cylindrical screwthreaded portion of the anchor member constituting the first screwthread, and a coaxial second screwthreaded portion, on the other side of the stop flange, constituting a second thread adapted to be screwed into bone.

Instead of this, or in addition to this, the anchor members may take the form of one or more hooks in which a rear wall of the hook, perpendicular to the axis of the cylindrical screwthreaded portion, serves as a stop flange.

The present invention is not limited to the embodiments explicitly described, but encompasses variants and generalizations thereof contained within the scope of the following claims.

The invention claimed is:

1. Device for treatment of the spine, comprising:
   anchor members (1, 2) adapted to be anchored in vertebrae, each having a cylindrical screwthreaded portion (5) onto which is screwed a clamping nut (8), and an anchor portion connected to the cylindrical screwthreaded portion (5) by an intermediate stop flange (7),
   at least one circular section securing rod (3) having a smooth exterior surface,
   sliding connecting members (4) for connecting the anchor members (1, 2) to the securing rod (3), the sliding connecting members (4) including a first hole (16) conformed to have the cylindrical screwthreaded portion (5) of an anchor member passed through it to fasten it to an anchor member, the sliding connecting members having a top transverse groove (17) conformed to receive a section of the securing rod (3), with clamping means for selectively clamping and unclamping the securing rod (3) in said transverse groove (17),
   wherein the clamping means comprise:
   a clamping screw (21), having a screwthreaded shank and a head,
   a clamping hole (20) in the bottom of the transverse groove of the sliding member, separate from the first hole (16) and offset laterally relative to the first hole (16),
   a cylindrical bearing surface (18) constituting a first edge of the transverse groove (17) and conformed to receive a section of the securing rod (3),
   an oblique bearing surface (19) constituting an opposite edge of the transverse groove (17) and inclined relative to the axis of the clamping hole,
   a clamping member (22) in the corner of the transverse groove (17) between the oblique bearing surface (19) and the securing rod (3) and adapted to be pushed toward the bottom of the transverse groove (17) by the clamping screw (21) in a first direction, the clamping member having a bearing face (22b) bearing and sliding on the oblique bearing surface (19) in a second direction, and having an opposite thrust face (22c) bearing on the securing rod (3) in a third direction, to immobilize it in the transverse groove (17), wherein both the second and third directions are non-parallel to said first direction.

2. Device according to claim 1 for treatment of the spine, wherein the clamping member (22) has a hole through it through which the clamping screw (21) passes, so that the head (21b) of the clamping screw (21) bears on the external face of the clamping member (22) to push it toward the bottom of the transverse groove (17).

3. Device according to claim 1 for treatment of the spine, wherein the clamping hole (20) is oriented obliquely to the axis (I) of the first hole (16), in the direction approaching the axis (I) of the first hole (16) on screwing of the clamping screw (21).

4. Device according to claim 1 for treatment of the spine, wherein the thrust face (22c) has a plane lower portion oriented generally toward the bottom of the transverse groove (17) to bear against the securing rod (3), and an upper portion open at the top to facilitate lateral engagement of the securing rod (3).

5. Device according to claim 1 for treatment of the spine, wherein the clamping member (22) turns freely about the clamping screw (21), and is retained axially on the screwthreaded shank (21a) of the clamping screw (21) by a flange (21c) of the clamping screw (21) engaged in an oval annular groove (22a) inside the hole in the clamping member (22).

6. Device according to claim 1 for treatment of the spine, wherein the stop flange (7) has a male spherical bearing surface (12) engaging in a corresponding female spherical surface (13) at the entry of the first hole (16) in the sliding connecting member (4), the first hole (16) in the sliding connecting member (4) having a diameter greater than the diameter of the cylindrical screwthreaded portion (5) of the anchor member to allow angular oscillation of the sliding connecting member (4) on the anchor member and away from the axis (I) before screwing of the clamping nut (8).

7. Device according to claim 1 for treatment of the spine, wherein the securing rod (3) is engaged, in the transverse groove (17), in an intermediate position between the clamping screw (21) and the anchor member (1, 2).

8. Device according to claim 1 for treatment of the spine, wherein the anchor members comprise one or more twin-thread bone screws (1), the cylindrical screwthreaded portion (5) of an anchor member constituting the first screwthread, and a coaxial second screwthreaded portion (9), on the opposite side of the stop flange (7), constituting a second screwthread adapted to screw into bone.

9. Device according to claim 1 for treatment of the spine, comprising anchor members in the form of one or more hooks (2) where the rear wall of a hook is perpendicular to the axis of the cylindrical screwthreaded portion (5), and serves as a stop flange.

10. Device for treatment of the spine, comprising:
    anchor members (1, 2) adapted to be anchored in vertebrae, each having a cylindrical screwthreaded portion (5) onto which is screwed a clamping nut (8), and an anchor portion connected to the cylindrical screwthreaded portion (5) by an intermediate stop flange (7),
    at least one circular section securing rod (3) having a smooth exterior surface,
    sliding connecting members (4) for connecting the anchor members (1, 2) to the securing rod (3), the sliding connecting members (4) including a first hole (16) conformed to have the cylindrical screwthreaded portion (5) of an anchor member passed through it to fasten it to an anchor member, the sliding connecting members having a top transverse groove (11) conformed to receive a section of the securing rod (3), with clamping means for selectively clamping and unclamping the securing rod (3) in said transverse groove (17),
    wherein the clamping means comprise:
    a clamping screw (21), having a screwthreaded shank and a head,
    a clamping hole (20) in the bottom of the transverse groove of the sliding member, separate from the first hole (16) and offset laterally relative to the first hole (16),
    a cylindrical bearing surface (18) constituting a first edge of the transverse groove (17) and conformed to receive a section of the securing rod (3),
    an oblique bearing surface (19) constituting an opposite edge of the transverse groove (17) and inclined relative to the axis of the clamping hole,
    a clamping member (22) in the corner of the transverse groove (17) between the oblique bearing surface (19)

and the securing rod (3) and adapted to be pushed toward the bottom of the transverse groove (17) by the clamping screw (21), having a bearing face (22*b*) bearing and sliding on the oblique bearing surface (19), and having an opposite thrust face (22*c*) bearing on the securing rod (3) to immobilize it in the transverse groove (17), wherein the thrust face (22*c*) has a plane lower portion oriented generally toward the bottom of the transverse groove (17) to bear against the securing rod (3), and an upper portion open at the top to facilitate lateral engagement of the securing rod (3).

11. Device for treatment of the spine, comprising:

anchor members (1, 2) adapted to be anchored in vertebrae, each having a cylindrical screwthreaded portion (5) onto which is screwed a clamping nut (8), and an anchor portion connected to the cylindrical screwthreaded portion (5) by an intermediate stop flange (7), at least one circular section securing rod (3) having a smooth exterior surface, sliding connecting members (4) for connecting the anchor members (1, 2) to the securing rod (3), the sliding connecting members (4) including a first hole (16) conformed to have the cylindrical screwthreaded portion (5) of an anchor member passed through it to fasten it to an anchor member, the sliding connecting members having a top transverse groove (17) conformed to receive a section of the securing rod (3), with clamping means for selectively clamping and unclamping the securing rod (3) in said transverse groove (17), wherein the clamping means comprise:

a clamping screw (21), having a screwthreaded shank and a head, a clamping hole (20) in the bottom of the transverse groove of the sliding member, separate from the first hole (16) and offset laterally relative to the first hole (16), a cylindrical bearing surface (18) constituting a first edge of the transverse groove (17) and conformed to receive a section of the securing rod (3), an oblique bearing surface (19) constituting an opposite edge of the transverse groove (17) and inclined relative to the axis of the clamping hole, a clamping member (22) in the corner of the transverse groove (17) between the oblique bearing surface (19) and the securing rod (3) and adapted to be pushed toward the bottom of the transverse groove (17) by the clamping screw (21), having a bearing face (22*b*) bearing and sliding on the oblique bearing surface (19), and having an opposite thrust face (22*c*) bearing on the securing rod (3) to immobilize it in the transverse groove (17), wherein the clamping member (22) turns freely about the clamping screw (21), and is retained axially on the screwthreaded shank (21*a*) of the clamping screw (21) by a flange (21*c*) of the clamping screw (21) engaged in an oval annular groove (22*a*) inside the hole in the clamping member (22).

\* \* \* \* \*